(12) United States Patent
Mehdizadeh et al.

(10) Patent No.: US 8,401,670 B2
(45) Date of Patent: Mar. 19, 2013

(54) NEUROLOGICAL SCREENING CONNECTOR

(75) Inventors: Bruce R. Mehdizadeh, Savage, MN (US); Farooq M. Francis, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 9 days.

(21) Appl. No.: 13/088,539

(22) Filed: Apr. 18, 2011

(65) Prior Publication Data

US 2011/0269350 A1 Nov. 3, 2011

Related U.S. Application Data

(60) Provisional application No. 61/329,771, filed on Apr. 30, 2010.

(51) Int. Cl.
*A61N 1/00* (2006.01)

(52) U.S. Cl. ............. 607/116; 607/2; 607/117; 439/638

(58) Field of Classification Search ...................... 607/37
See application file for complete search history.

(56) References Cited

U.S. PATENT DOCUMENTS

| | | | |
|---|---|---|---|
| 5,683,433 A * | 11/1997 | Carson | 607/36 |
| 2003/0120327 A1* | 6/2003 | Tobritzhofer et al. | 607/116 |
| 2005/0027326 A1* | 2/2005 | Ries et al. | 607/37 |
| 2006/0167522 A1* | 7/2006 | Malinowski | 607/37 |
| 2007/0049985 A1* | 3/2007 | Kessler et al. | 607/37 |
| 2008/0255630 A1* | 10/2008 | Arisso et al. | 607/37 |
| 2008/0269831 A1* | 10/2008 | Erickson | 607/37 |
| 2009/0018601 A1* | 1/2009 | Deininger et al. | 607/37 |

* cited by examiner

*Primary Examiner* — Christopher D Koharski
*Assistant Examiner* — Michael Carey

(57) ABSTRACT

A medical lead screening connector includes a first housing portion having a first lead receptor channel and a second housing portion having a second lead receptor channel and the second housing portion is pivotally connected to the first housing portion. The first lead receptor channel includes two first contact apertures and the second lead receptor channel comprising two second contact apertures. The first housing portion includes two second lead receptor contacts that mate with the second contact apertures and the second housing portion includes two first lead receptor contacts that mate with the first contact apertures.

19 Claims, 5 Drawing Sheets

NEUROLOGICAL SCREENING CONNECTOR

The present application claims priority to U.S. Provisional Patent Application No. 61/329,771, filed Apr. 30, 2010, which application is hereby incorporated by reference as if re-written in its entirety.

BACKGROUND

The medical device industry produces a wide variety of electronic and mechanical devices for treating patient medical conditions such as pacemakers, defibrillators, neurostimulators and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life.

One type of medical device is an implantable neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an extension. The neurostimulator can be connected to a stimulation lead that has one or more electrodes to deliver electrical stimulation to a specific location in the patient's body.

The lead and stylet combination are part of an implantable neurostimulation system. The neurostimulation lead is placed in the desired location of the body. The stylet wire and handle combination are used to give the lead stiffness during implantation and to aid in maneuvering the lead into the desired position. Once the lead is believed to be placed in the appropriate position within the body the lead, with or without the stylet, is coupled with a neurostimulation screening cable, which is connected to a neurostimulation screening device. The screening device can be programmed to send different combinations, strengths and frequencies of electrical stimulation to the patient. The screening cable provides a connection to, and electrical pathway between the stimulation lead or percutaneous extension and the neurostimulation screening device. The patient is questioned to determine if the stimulation covers the desired region of the body. Provided results are favorable the patient receives a temporary implant of the stimulation lead system. Either the stimulation lead or percutaneous extension is attached to the screening cable for a trial screening period so the patient can assess the efficacy of the system in normal life settings. The patient can be sent home with an external neurostimulator that sends electrical stimulation to the stimulation lead via the screening cable during the trial period. This trial period can range from 1 to 30 days depending on the physician and the country in which the trial occurs. This trial period is used to access the efficacy of the stimulation therapy for the patient.

BRIEF SUMMARY

The present disclosure relates to a medical lead screening connector. In particular, the present disclosure relates to a medical lead screening connector that includes two opposing housing portions that are pivotally connected and electrical contacts of an opposing housing makes electrical contact with a lead body of the opposing housing.

In one illustrative embodiment, a medical lead screening connector includes a first housing portion having a first lead receptor channel and a second housing portion having a second lead receptor channel and the second housing portion is pivotally connected to the first housing portion. The first lead receptor channel includes two first contact apertures and the second lead receptor channel comprising two second contact apertures. The first housing portion includes two second lead receptor contacts that mate with the second contact apertures and the second housing portion includes two first lead receptor contacts that mate with the first contact apertures.

In another embodiment, a medical lead screening connector includes a first housing portion including two first lead receptor channels and a second housing portion including two second lead receptor channels. Each of the first lead receptor channels include two first contact apertures and each of the second lead receptor channels include two second contact apertures. The second housing portion is pivotally connected to the first housing portion. The first housing portion includes two second lead receptor contacts that mate with the second contact apertures when the first and second housing portions are in the closed position and the second housing portion includes two first lead receptor contacts that mate with the first contact apertures when the housing is in the open position.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
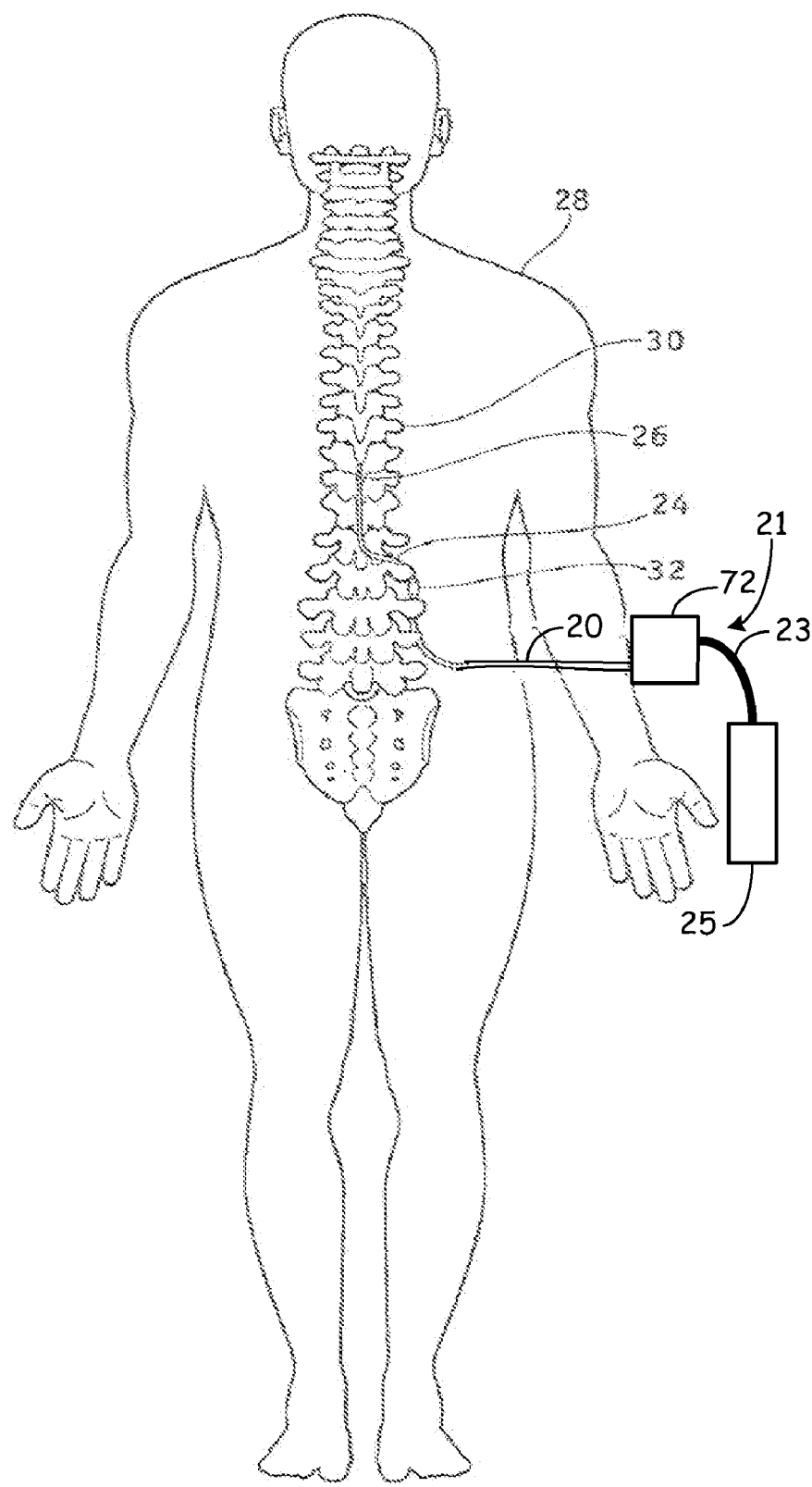
FIG. 1 is a schematic diagram of a neurological lead implanted within a human body or patient.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise As used in this specification and the appended claims, the term "or" is generally employed in its sense including "and/or" unless the content clearly dictates otherwise. Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if a cell depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to a medical lead screening connector. In particular, the present disclosure relates to a medical lead screening connector. In particular, the present disclosure relates to a medical lead screening connector that includes two opposing housing portions that are pivotally connected and electrical contacts of an opposing housing makes electrical contact with a lead body of the opposing housing. This design can be described as a "clamshell" type design where the two housing portions are hingedly connected and make electrical contact upon closing the two opposing housing portions. Axial lead insertion can be accomplished with nearly zero force. In addition, contacts present on the lead body can be viewed through the contact apertures when the housings are in the open position. While the present disclosure is not so limited, an appreciation of various aspects of the disclosure will be gained through a discussion of the examples provided below.

The teachings presented herein are applicable to any implantable medical device system employing a lead for delivering electrical signals to a tissue of a patient. For example, the system may include a neurostimulator, such as a peripheral nerve stimulator, a spinal cord stimulator, or a deep brain stimulator; a cardiac pacemaker or defibrillator; a gastric stimulator; or the like. It will be understood that the systems and devices described herein may be readily applied to systems employing leads for purposes of screening, sensing, monitoring, recording, or the like.

FIG. 1 is a schematic diagram of a neurological lead 24 implanted within a human body or patient 28. The implanted neurological lead 24 is a medical wire with special insulation. The neurological lead 24 includes one or more insulated electrical conductors with a connector on the proximal end and electrical contacts on the distal end. Some neurological leads are designed to be inserted into a patient percutaneously, and some neurological leads are designed to be surgically implanted. The neurological lead 24 may also be a paddle having a plurality of electrodes. Those skilled in the art will appreciate that any variety of neurological leads 24 may be used.

The neurological lead 24 can be implanted and positioned to stimulate a specific site in the spinal cord 30 or the nervous system. The neurological lead 24 includes one or more electrodes 26 (small electrical contacts) through which electrical stimulation is delivered from either an external stimulator 25 or an implanted stimulator (not shown) to the targeted neural tissue. The external stimulator 25 or an implanted stimulator can be any "active medical device" or "signal generator" as described above and can be placed external to or in any location within a body cavity or tissue within the body, or on the surface of a patient's skin, as desired.

The external stimulator 25 can be used to test the efficacy of stimulation therapy for the patient before an implantable stimulator is surgically implanted. The external stimulator 25 is used in conjunction with a screening cable 21 which accepts the stimulation lead 24 or lead extension 20 and creates an electrical pathway to the external stimulator 25. The screening cable 21 includes a conductor cable 23 and a distal screening connector 72 that includes pivoting lead receptacles (described below). The conductor cable 23 electrically connects the lead receptacles within the distal screening connector 72 to the external stimulator 25.

The illustrated external stimulator 25 is coupled to a lead extension 20 via the screening cable 21. The lead extension 20 has a proximal end coupled to the screening cable 21, and a lead 24 having a proximal end coupled to a distal end 32 of the lead extension 20 and a distal end of the lead 24 coupled to one or more electrodes 26. In some embodiments, the lead 24 proximal end is coupled to the screening cable 21, without a need for a lead extension. In many embodiments, the screening cable 21 couples to one or two or more leads each having four to eight electrodes. Such a system may also include a physician programmer and a patient programmer (not shown). The external stimulator 25 can be considered to be a signal generator of the type available from Medtronic, Inc., and capable of generating multiple signals occurring either simultaneously or one signal shifting in time with respect to the other, and having independently varying amplitudes and signal widths. The external stimulator 25 can contain a power source and the electronics for sending precise, electrical signals to the patient to provide the desired treatment therapy. While the external stimulator 25, in many embodiments, provides electrical stimulation by way of signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously, and some are designed to be surgically implanted. In some embodiments, the lead 24 may contain a paddle at its distant end for housing electrodes 26. In many embodiments, electrodes 26 may include one or more ring contacts at the distal end of lead 24.

Figure 2:
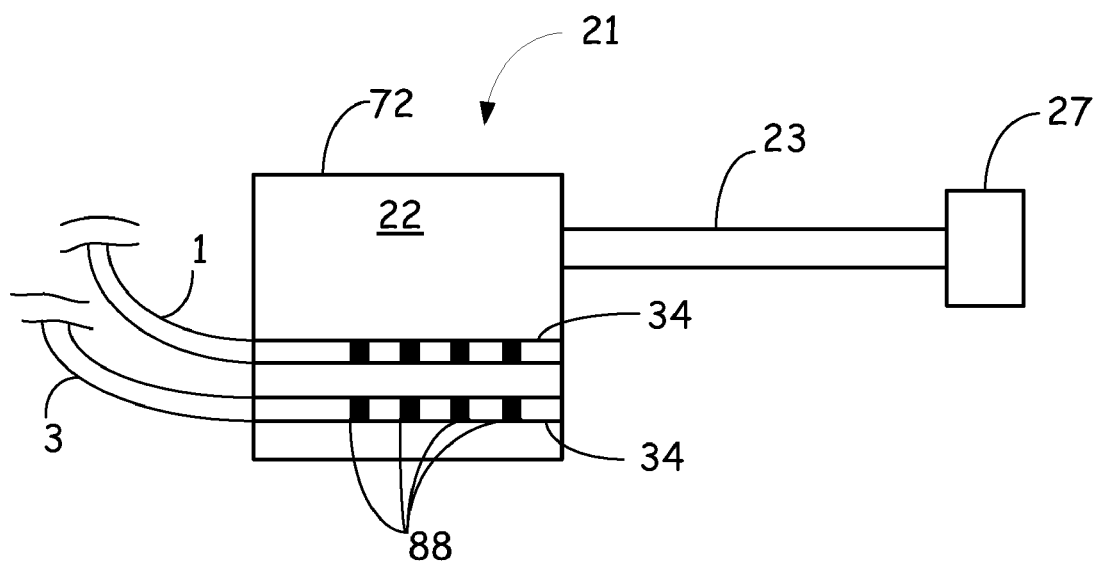
FIG. 2 is a schematic diagram of an illustrative screening cable.

FIG. 2 is a schematic diagram of an illustrative screening cable 21. The screening cable 21 includes a proximal screening connector 27 electrically coupled to lead receptacles 34 in the lead connector housing 22 of the distal screening connector 72. Conductor wires are disposed within the conductor cable 23 electrically coupled the lead receptacles 34 to the proximal screening connector 27. While two lead receptacles are illustrated, it is understood that the distal screening connector 72 can include any number of lead receptacles, as desired. In some embodiments, the distal screening connector 72 can be directly electrically coupled to a lead screening device or programming device (e.g., external stimulation device).

A first implantable medical lead 1 and second implantable medical lead 3 are received in the lead receptacles 34. The lead receptors 34 are configured for receiving the first implantable medical lead 1 and a second implantable medical lead 3. Electrical contacts on the lead 1, 3 mates with electrical contacts 88 within the distal screening connector 72.

The first implantable medical lead 1 and a second implantable medical lead 3 can be a wide variety of medical leads, such as a neurological lead. In some embodiments the medical lead can be a four-conductor neurological lead, a four-conductor extension, a four-conductor neurological lead with stylet handle, a four conductor percutaneous extension with stylet handle, an eight-conductor neurological lead, an eight-conductor extension, an eight-conductor neurological lead with stylet handle, and the like.

Figure 3:
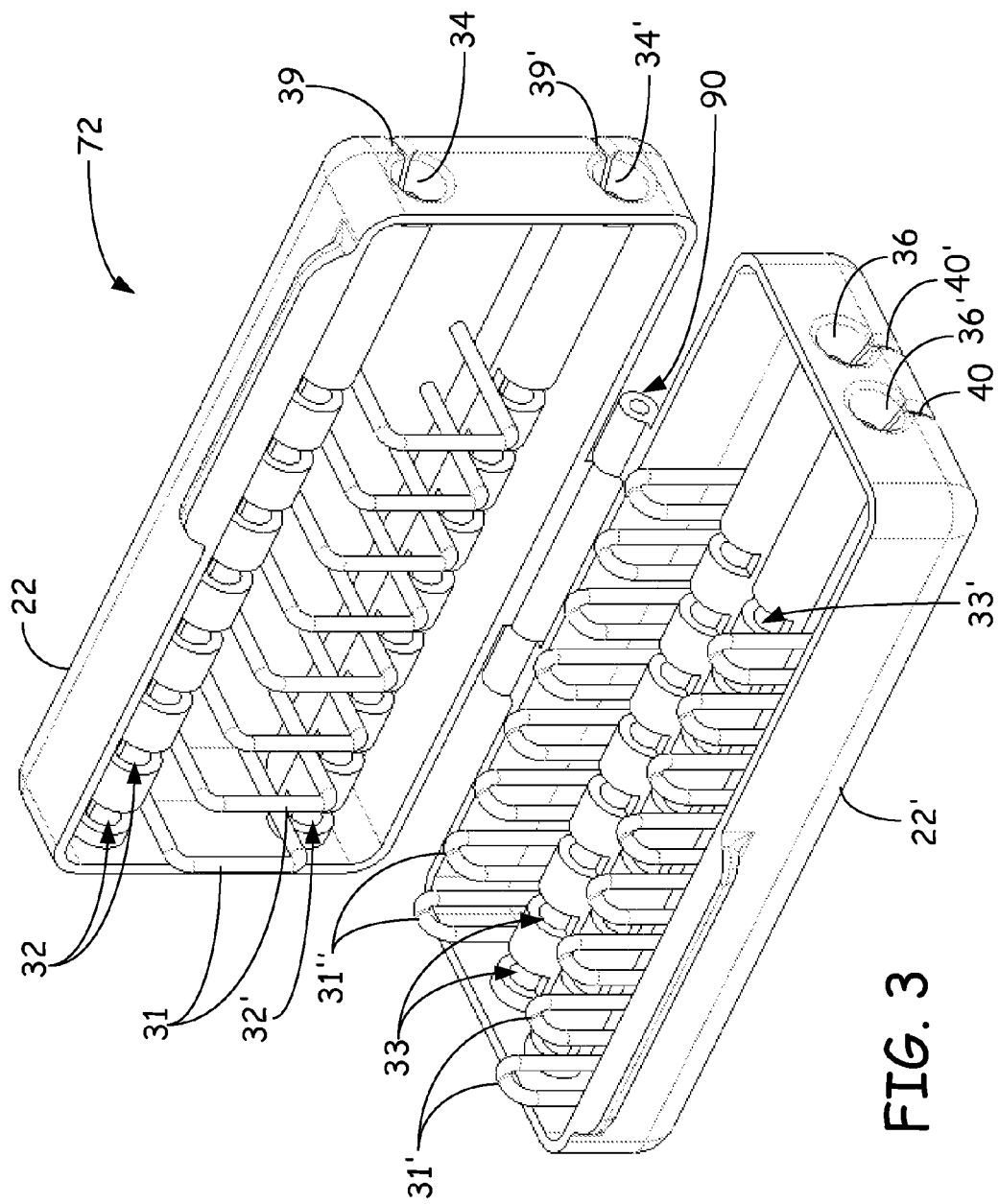
FIG. 3 is a schematic diagram perspective view of an illustrative, screening cable housing in the open position.
Figure 4:
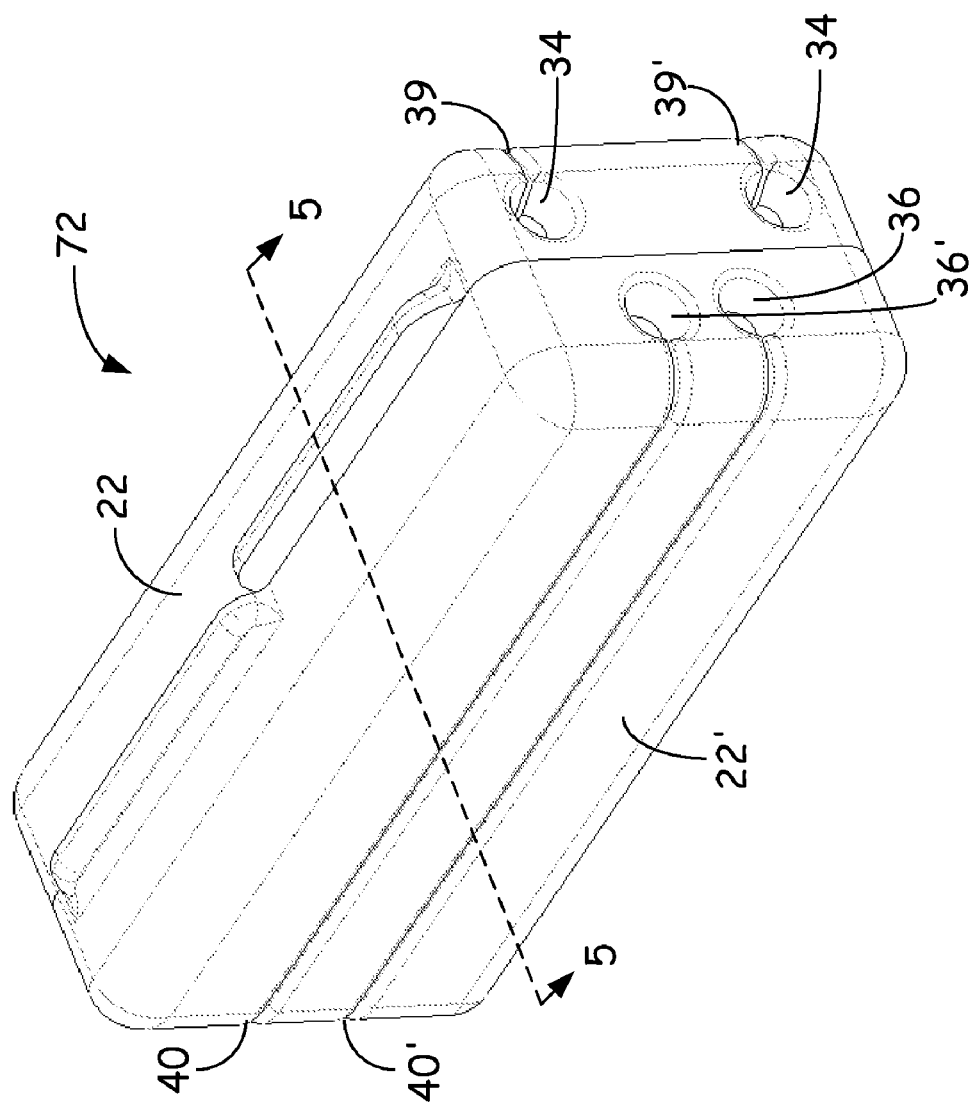
FIG. 4 is a schematic diagram rear view of the illustrative screening cable housing in the closed position.
Figure 5:
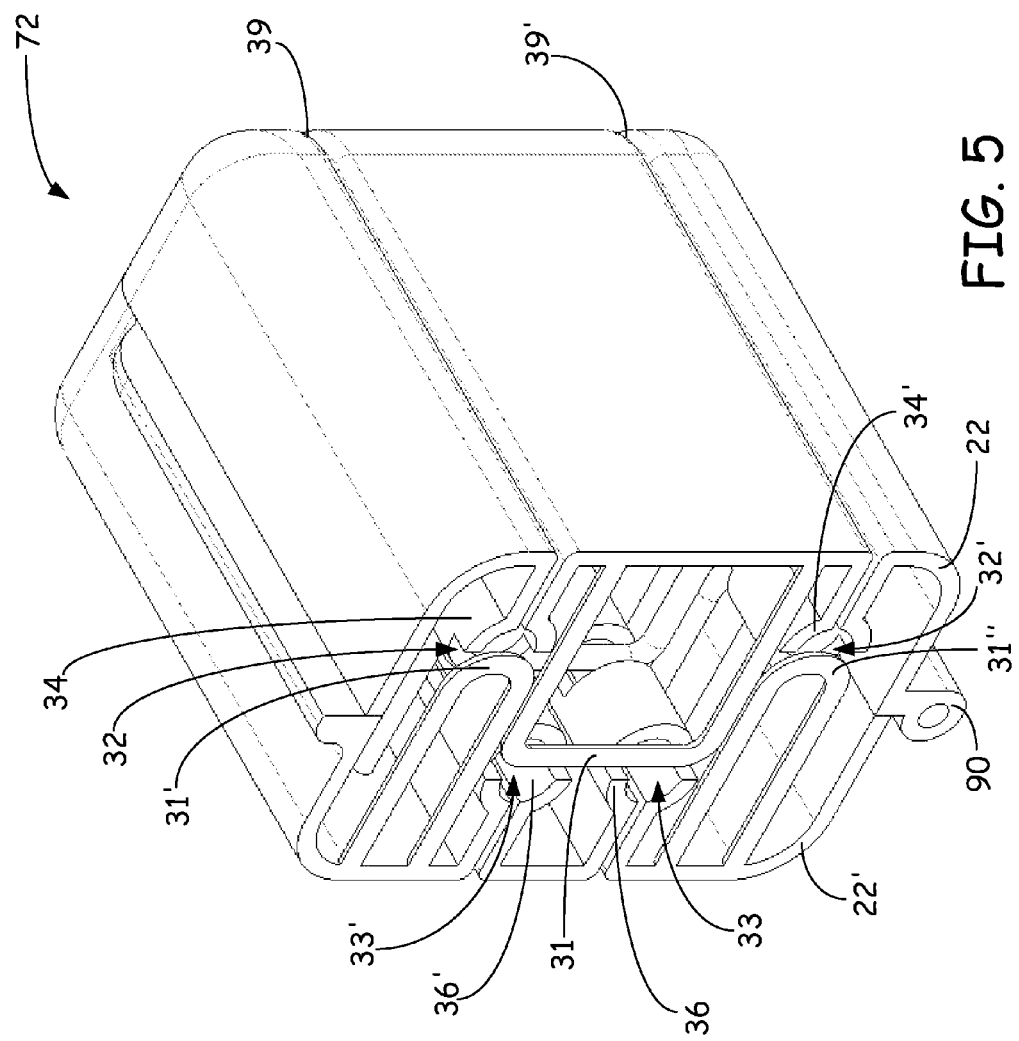
FIG. 5 is a perspective cross-sectional schematic diagram of an illustrative screening cable with the cover of the lead screening connector of FIG. 4 taken along lines 5-5.

FIG. 3 is a schematic diagram perspective view of an illustrative screening cable housing in the open position. FIG. 4 is a schematic diagram rear view of the illustrative screening cable housing in the closed position. FIG. 5 is a perspective cross-sectional schematic diagram of an illustrative screening cable with the cover of the lead screening connector of FIG. 4 taken along lines 5-5.

In one illustrative embodiment, a medical lead screening connector 72 includes a first housing portion 22 having a first lead receptor channel 34 and a second housing portion 22' having a second lead receptor channel 36. The second housing portion 22' is pivotally connected to the first housing portion 22 via a hinge 90. The first lead receptor channel 34 includes two first contact apertures 32 and the second lead receptor channel 36 includes two second contact apertures 33. The first housing portion 22 includes two second lead receptor contacts 31 that mate with the second contact apertures 33 and the second housing portion 22' includes two first lead receptor contacts 31' that mate with the first contact apertures 32.

In another embodiment, a medical lead screening connector 72 includes a first housing portion 22 including two first lead receptor channels 34, 34' and a second housing portion 22' including two second lead receptor channels 36, 36'. Each of the first lead receptor channels 34, 34' include two first contact apertures 32, 32' and each of the second lead receptor channels 36, 36' include two second contact apertures 33, 33'. The second housing portion 22' is pivotally connected to the first housing portion 22 via a hinge 90. The first housing portion 22 includes two second lead receptor contacts 31 that mate with the second contact apertures 33, 33' when the first and second housing portions 22, 22' are in the closed position (see FIG. 4) and the second housing portion 22' includes two first lead receptor contacts 31', 31" that mate with the first contact apertures 32, 32' when the housing is in the closed position (see FIG. 3).

The two second lead receptor contacts 31 are arranged and configured to electrically contact a lead body received in the second lead receptor channel 36, 36' through the two second contact apertures 33, 33'. The two first lead receptor contacts 31', 31" are arranged and configured to electrically contact a lead body received in the fist lead receptor channel 34, 34' through the two second contact apertures 32, 32'.

In many embodiments, the two second lead receptor contacts 31 are disposed between the two first lead receptor channels 34, 34'. In many embodiments, the two second lead receptor channels 36, 36' are disposed between the two first lead receptor contacts 31' 31". The screening cable 21 (see FIG. 2) includes a proximal screening connector 27 electrically coupled to first lead receptor contacts 31', 31" and second lead receptor contacts 31 in the screening connector 72. Conductor wires are disposed within the conductor cable 23 and electrically coupled to the first lead receptor contacts 31', 31" and second lead receptor contacts 31 to the proximal screening connector 27. While four eight contact lead receptacles are illustrated in FIG. 3 to FIG. 5, it is understood that the distal screening connector 72 can include any number of lead receptacles, as desired. The distal screening connector 72 can be directly electrically coupled to a lead screening device or programming device (e.g., external stimulation device 25, see FIG. 1) via the proximal screening connector.

The second housing portion 22' and the first housing portion 22 can articulate at least 90 degrees relative to each other between an open position (FIG. 3) and closed position (FIG. 4). In some embodiments, the second housing portion 22' and the first housing portion 22 can articulate at least 170 degrees relative to each other between an open position (FIG. 3) and closed position (FIG. 4). In some embodiments, the second housing portion 22' and the first housing portion 22 can articulate at least 180 degrees relative to each other between an open position (FIG. 3) and closed position (FIG. 4).

In many embodiments a slit 39, 39' extends along a length of the first lead receptor channels 34, 34'. The slit 39, 39' is configured to allow an element to pass between the exterior of the first housing portion 22 and the first lead receptor channels 34, 34' interior. The slit 39, 39' can be utilized to allow a wire or stylet associated with a lead to travel through the slit 39, 39' as the lead body is received in the first lead receptor channels 34, 34'. Likewise, a slit 40, 40' extends along a length of the second lead receptor channels 36, 36'. The slit 40, 40' is configured to allow an element to pass between the exterior of the second housing portion 22' and the second lead receptor channels 36, 36' interior. The slit 40, 40' can be utilized to allow a wire or stylet associated with a lead to travel through the slit 40, 40' as the lead body is received in the second lead receptor channels 36, 36'.

Thus, embodiments of the NEUROLOGICAL SCREENING CONNECTOR are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A medical lead screening connector comprising:
   a first housing portion comprising a first lead receptor channel, the first lead receptor channel comprising two first contact apertures; and
   a second housing portion comprising a second lead receptor channel, the second lead receptor channel comprising two second contact apertures, and the second housing portion pivotally connected to the first housing portion;
   wherein the first housing portion comprises two second lead receptor contacts that mate with the second contact apertures and the second housing portion comprises two first lead receptor contacts that mate with the first contact apertures.

2. A medical lead screening connector according to claim 1, wherein the second housing portion and the first housing portion can articulate at least 180 degrees relative to each other between an open and closed position.

3. A medical lead screening connector according to claim 2, wherein the two second lead receptor contacts electrically contacts a lead body received in the second lead receptor channel.

4. A medical lead screening connector according to claim 3, wherein the two second lead receptor contacts electrically contacts a lead body received in the second lead receptor channel through the two second contact apertures.

5. A medical lead screening connector according to claim 4, wherein the two first lead receptor contacts electrically contacts a lead body received in the first lead receptor channel.

6. A medical lead screening connector according to claim 5, wherein the two first lead receptor contacts electrically contacts a lead body received in the first lead receptor channel through the two first contact apertures.

7. A medical lead screening connector according to claim 3, wherein the two second lead receptor contacts electrically contacts a lead body received in the second lead receptor channel when the medical lead screening connector is in a closed position and the two second lead receptor contacts do not electrically contact a lead body received in the second lead receptor channel when the medical lead screening connector is in an open position.

8. A medical lead screening connector according to claim 7, wherein the two first lead receptor contacts electrically contacts a lead body received in the first lead receptor channel when the medical lead screening connector is in a closed position and the two first lead receptor contacts do not electrically contact a lead body received in the first lead receptor channel when the medical lead screening connector is in an open position.

9. A medical lead screening connector according to claim 8, wherein the first housing portion comprises two first lead receptor channels.

10. A medical lead screening connector according to claim 9, wherein the second housing portion comprises two second lead receptor channels.

11. A medical lead screening connector according to claim 10, wherein the two second lead receptor contacts are disposed between the two first lead receptor channels.

12. A medical lead screening connector according to claim 11, wherein the two second lead receptor channels are disposed between the two first lead receptor contacts.

13. A medical lead screening connector according to claim 12, wherein the first lead receptor contacts and the second lead receptor contacts are electrically connected to an external stimulator via the medical lead screening connector.

14. A medical lead screening connector comprising:
a first housing portion comprising two first lead receptor channels, each of the first lead receptor channels comprising two first contact apertures; and
a second housing portion comprising two second lead receptor channels, each of the second lead receptor channels comprising two second contact apertures, and the second housing portion pivotally connected to the first housing portion;
wherein the first housing portion comprises two second lead receptor contacts that mate with the second contact apertures when the first and second housing portions are in the closed position and the second housing portion comprises two first lead receptor contacts that mate with the first contact apertures when the housing is in the closed position.

15. A medical lead screening connector according to claim 14, wherein the two second lead receptor contacts are disposed between the two first lead receptor channels.

16. A medical lead screening connector according to claim 15, wherein the two second lead receptor channels are disposed between the two first lead receptor contacts.

17. A medical lead screening connector according to claim 16, wherein the two second lead receptor contacts electrically contacts a lead body received in either of the second lead receptor channels through the two second contact apertures.

18. A medical lead screening connector according to claim 17, wherein the two first lead receptor contacts electrically contacts a lead body received in either of the first lead receptor channels through the two first contact apertures.

19. A medical lead screening connector according to claim 18, wherein the first lead receptor contacts and the second lead receptor contacts are electrically connected to an external stimulator via the medical lead screening connector.

* * * * *